(12) United States Patent
Vidarsson et al.

(10) Patent No.: US 8,426,141 B2
(45) Date of Patent: Apr. 23, 2013

(54) METHODS FOR INCREASING THE THERAPEUTIC EFFICACY OF IMMUNOGLOBULIN G CLASS 3 (IGG3) ANTIBODIES

(75) Inventors: Gestur Vidarsson, Maarssen (NL); Catherine E. Van der Schoot, Badhoevedorp (NL)

(73) Assignee: Stichting Sanquin Bloedvoorziening (NL)

( * ) Notice: Subject to any disclaimer, the term of this patent is extended or adjusted under 35 U.S.C. 154(b) by 214 days.

(21) Appl. No.: 12/809,981

(22) PCT Filed: Jan. 18, 2008

(86) PCT No.: PCT/EP2008/000373
§ 371 (c)(1),
(2), (4) Date: Sep. 7, 2010

(87) PCT Pub. No.: WO2009/089846
PCT Pub. Date: Jul. 23, 2009

(65) Prior Publication Data
US 2011/0003336 A1    Jan. 6, 2011

(51) Int. Cl.
*G01N 33/53* (2006.01)
*G01N 33/567* (2006.01)
*C12P 21/06* (2006.01)
*C07K 16/00* (2006.01)

(52) U.S. Cl.
USPC ........... 435/7.1; 435/7.2; 435/7.21; 435/7.24; 435/7.8; 435/69.1

(58) Field of Classification Search .................. None
See application file for complete search history.

(56) References Cited

U.S. PATENT DOCUMENTS

| 6,277,375 B1 * | 8/2001 | Ward | 424/133.1 |
| 2006/0134105 A1 * | 6/2006 | Lazar et al. | 424/133.1 |
| 2008/0138335 A1 * | 6/2008 | Takahashi et al. | 424/133.1 |

FOREIGN PATENT DOCUMENTS

| EP | 1847602 | | 1/2008 |
| WO | WO 2006/075668 | * | 7/2006 |

OTHER PUBLICATIONS

Jendeberg et al. Journal of Immunological Methods 201 (1997) 25-34.*
Asai et al., "An interaction between S*tag and S*protein derived from human ribonuclease 1 allows site-specific conjugation of an enzyme to an antibody for targeted drug delivery" Journal of Immunological Methods 299 (2005) 63-76.
Burton et al., "Human Antibody Effector Function" Advances in Immunology, vol. 51 (1992) 51:1-84.
Fipula et al., "Antibody engineering and modification technologies" Biomolecular Engineering 24 (2007) 201-215.
Kim et al., "Mapping the site on human IgG for binding of the MHC class I-related receptor, FcRn" Eur. J. Immunol. (1999) 29:2819-2825.
Lewis et al., "The different effector function capabilities of the seven equine IgG subclasses have implications for vaccine strategies" Molecular Immunology 45 (2008) 818-827.
Sauer-Eriksson et al., "Crystal structure of the C2 fragment of streptococcal protein G in complex with the Fc domain of the human IgG"; Structure (1995) vol. 3 No. 3:265-278.
Tabrizi et al., "Elimination mechanisms of therapeutic monoclonal antibodies" DDT vol. 11, No. 1/2 (2006) pp. 81-88.
Vidarsson et al., "FcRn: an IgG receptor on phagocytes with a novel role in phagocytosis" Blood (2006) vol. 108, No. 10; pp. 3573-3579.

* cited by examiner

*Primary Examiner* — Chun Dahle
(74) *Attorney, Agent, or Firm* — Bret E. Field; Louis-Vu T. Nguyen; Bozicevic, Field & Francis LLP (57) ABSTRACT

The present invention relates to methods for increasing the therapeutic efficacy of immunoglobulin G class 3 (IgG3) antibodies, immunoglobulin G class 3 (IgG3) antibodies with an improved therapeutic efficacy and the use thereof as a medicament, in particularly a medicament for immunotherapy. Specifically, the present invention relates to methods for increasing the therapeutic efficacy of an immunoglobulin G class 3 (IgG3) antibody comprising providing a mutated immunoglobulin G class 3 (IgG3) antibody, wherein the mutation, as compared to the parent immunoglobulin G class 3 (IgG3) antibody, comprises a replacement of the amino acid arginine (R) at position 435 in the $C_H3$ domain with the amino acid histidine (H), and antibodies obtained by the present methods and their use as a medicament.

3 Claims, 6 Drawing Sheets

SEQUENCE LISTING

```
<160> NUMBER OF SEQ ID NOS: 7

<210> SEQ ID NO 1
<211> LENGTH: 31
<212> TYPE: DNA
<213> ORGANISM: Artificial
<220> FEATURE:
<223> OTHER INFORMATION: amplification primer 1 for human FcRn cDNA

<400> SEQUENCE: 1
ggatccacca tggggtccc gcggcctcag c                                    31

<210> SEQ ID NO 2
<211> LENGTH: 27
<212> TYPE: DNA
<213> ORGANISM: Artificial
<220> FEATURE:
<223> OTHER INFORMATION: amplification primer 2 for human FcRn cDNA

<400> SEQUENCE: 2
gaattctcag gcggtggctg gaatcac                                        27

<210> SEQ ID NO 3
<211> LENGTH: 34
<212> TYPE: DNA
<213> ORGANISM: Artificial
<220> FEATURE:
<223> OTHER INFORMATION: site-directed mutagenesis primer IgG1-H435R

<400> SEQUENCE: 3
```

```
gaggctctgc acaaccgcta cacgcagaag agcc                34

<210> SEQ ID NO 4
<211> LENGTH: 34
<212> TYPE: DNA
<213> ORGANISM: Artificial
<220> FEATURE:
<223> OTHER INFORMATION: site-directed mutagenesis primer IgG3-R435A

<400> SEQUENCE: 4
gaggctctgc acaacgccta cacgcagaag agcc                34

<210> SEQ ID NO 5
<211> LENGTH: 34
<212> TYPE: DNA
<213> ORGANISM: Artificial
<220> FEATURE:
<223> OTHER INFORMATION: site-directed mutagenesis primer IgG3-R435H

<400> SEQUENCE: 5
gaggctctgc acaaccacta cacgcagaag agcc                34

<210> SEQ ID NO 6
<211> LENGTH: 24
<212> TYPE: DNA
<213> ORGANISM: Artificial
<220> FEATURE:
<223> OTHER INFORMATION: Z-domain forward amplification primer

<400> SEQUENCE: 6
ggatccgtag acaacaaatt caac                           24

<210> SEQ ID NO 7
<211> LENGTH: 27
<212> TYPE: DNA
<213> ORGANISM: Artificial
<220> FEATURE:
<223> OTHER INFORMATION: Z-domain reverse amplification primer

<400> SEQUENCE: 7
ctgcagttat ttcggcgcct gagcatc                        27
```

METHODS FOR INCREASING THE THERAPEUTIC EFFICACY OF IMMUNOGLOBULIN G CLASS 3 (IGG3) ANTIBODIES

The present invention relates to methods for increasing the therapeutic efficacy of immunoglobulin G class 3 (IgG3) antibodies, immunoglobulin G class 3 (IgG3) antibodies with an improved therapeutic efficacy and the use thereof as a medicament, in particularly a medicament for immunotherapy.

Before infants acquire their own adaptive antibody mediated immunity, they are protected by maternal antibodies of the IgG class, which are actively transferred from mother to child. This intra-uterine IgG transport across the placenta in humans, or (e.g. in rodents) after birth from mothers milk across the intestinal epithelium, is mediated by the neonatal Fc-receptor (FcRn).

FcRn is a heterodimer consisting of a unique HLA class-I like α-chain, associated with β2M. FcRn binds IgG with high affinity at acidic pH (approximately 6.5), but binding is almost entirely abrogated at physiological pH (approximately 7.4).

In vivo, binding is presumed to take place in early endosomes after pinocytosis of plasma containing IgG. FcRn-IgG complexes are formed and routed away from the lysosomal pathway, probably due to various sorting signals in the cytoplasmic tail of FcRn.

These complexes are either recycled to the cell surface or transported to the opposite side of the cell, where the vesicles containing FcRn-IgG complexes either fuse with the plasma membrane in one go, or in a series of "kiss and run" events. During these events, the pH returns to physiological levels (approximately 7.4), which strongly reduces the affinity of FcRn for IgG. This causes the complex to dissociate and IgG is released while FcRn is presumed to be recycled to reassociate with IgG.

Apart from IgG transport, FcRn mediates various other functions. For example, it rescues albumin from lysosomal degradation and was shown to play a role in phagocytosis.

As a salvage receptor for IgG, FcRn is believed to be responsible for the high plasma concentrations (approximately 10 mg/ml for total IgG) of IgG1, IgG2 and IgG4. However, it is not clear whether FcRn binds, transports and rescues IgG3 in a similar manner, as the serum half life of IgG3 is only a fraction of that of other IgG subclasses and is comparable to that of other serum proteins (IgG3 approximately 7 days versus IgG1, IgG2 and IgG4 approximately 21 days). There are at least two possible theories for this observed serum half life of IgG3.

Firstly, the relatively long hinge region of IgG3 makes it more accessible to the activity of proteolytic enzymes like papain, plasmin, trypsin and/or pepsin.

Secondly, the recycling of IgG3 by FcRn, if any, may be less efficient than that of other IgG subclasses.

As compared to IgG1 antibodies, commonly used for immunotherapy, IgG3 antibodies provide improved therapeutic effects with respect to, amongst others, antibody-dependent cell-mediated cytotoxicity (ADCC), phagocytosis, and/or complement activation making IgG3 a more suitable candidate for antibody based therapies.

However, the relatively short half life of IgG3 antibodies, as compared to IgG1 antibodies, has severely limited their therapeutic application, despite these therapeutic advantageous properties.

Therefore, it is an object of the present invention to provide IgG3 antibodies with an increased therapeutic efficacy, and especially IgG3 antibodies with an increased serum half life comparable to the serum half life of IgG1 antibodies.

This object, amongst other objects, is met by a method as outlined in appended claim 1.

Specifically, this object is met by a method for increasing the therapeutic efficacy of an immunoglobulin G class 3 (IgG3) antibody comprising providing a mutated immunoglobulin G class 3 (IgG3) antibody, wherein the mutation, as compared to the parent immunoglobulin G class 3 (IgG3) antibody, comprises a replacement of the amino acid arginine (R) at position 435 in the $C_H3$ domain with the amino acid histidine (H). Such mutation is also designated in the art of antibody engineering as a R435H mutation.

The term "a mutated immunoglobulin G class 3 (IgG3) antibody" or "a mutated IgG3", as used interchangeably herein, indicates an IgG3 antibody not found in nature, or derivable using conventional antibody raising and isolating techniques such as polyclonal or hybridoma technology.

The present "a mutated immunoglobulin G class 3 (IgG3) antibody" or "a mutated IgG3" is derived using common recombinant DNA technology on nucleic acid material originating from antibodies, herein designated by the term "parent", for example, obtained through conventional antibody raising and isolating techniques. However, the present antibody differs from these "parent" antibodies in its therapeutic efficacy, and especially its serum half life.

In a particularly preferred embodiment of the present invention, the present mutated IgG3, as compared to the parent IgG3, providing a source of nucleic acid material to be mutated to provide the present mutated IgG3, has all characterizing features, such as affinity and specificity, of the parent IgG3, and differs only in that the therapeutic efficacy, and especially the serum half life, is increased.

Surprisingly it was found by the present inventors that the presence of a histidine (H) residue at position 435 in an IgG3 heavy chain increases the in vivo serum half life of an IgG3 antibody to levels comparable to the in vivo half life of IgG1, IgG2 and IgG4 antibodies, i.e., approximately 21 days.

This effect is surprising because previous studies, as the present example, have shown that the individual transport efficiency of both IgG1, having a histidine residue at position 435, and IgG3, having an argine residue at position 435, by FcRn receptor are comparable.

Without wishing to be bound to any theory, the underlying increased serum half life of the present IgG3 antibody, i.e., IgG3(R435H), is assumed to be provided by abolishing a competition between IgG1 and IgG3 for the FcRn receptor. In vivo, both IgG1 and IgG3 are present in serum, but by competing for the FcRn receptor, and the subsequent cellular rescue of lysosomal degradation in favor of IgG1, IgG1 remains in the circulation for approximately 21 days, while IgG3 is quickly degraded at a similar rate as other serum proteins, i.e., approximately 7 days.

Conversion of the arginine (R) residue at position 435 of IgG3 to a histidine (H) residue abolishes this competition advantage of IgG1 compared to IgG3, thereby increasing the serum half life of IgG3 to a half life comparable to that of IgG1, IgG2 and/or IgG4.

According to the present invention, amino acid position 435 of an IgG3 antibody is amino acid position 435 of the heavy chain $C_H3$ domain of an IgG3 antibody according to the Kabat amino acid residue position designation.

However, the present invention also encompasses other arginine (R) to histidine (H) replacements at positions corresponding, or equivalent, to position 435 of the heavy chain $C_H3$ domain of an IgG3 antibody according to the Kabat designation.

The present IgG3 antibody is mutated as compared to the parent IgG3 antibody. In general, the present parent IgG3 antibody exhibits a serum half life of approximately 7 days and comprises a arginine at position 435. The present IgG3 antibody preferably exhibits a similar affinity and specificity as the parent IgG3 antibody except that its half life is increased from approximately 7 days to approximately 21 days, due to the R435H mutation.

In a preferred embodiment, the present IgG3 antibody has a substantially similar amino sequence as the parent IgG3 antibody, more preferably a substantially identical amino acid sequence, and most preferably an identical amino acid sequence, except for the R435H mutation.

Because of the above most preferable embodiment, the present invention also relates to a method for providing a mutated IgG3 antibody wherein the mutation, as compared to the parent IgG3 antibody, consists of a replacement of the amino acid arginine (R) at position 435 in the $C_H3$ domain with the amino acid histidine (H).

In a preferred embodiment, the IgG3 antibody according to the present method is a human IgG3 antibody. Within the context of the present invention, a human antibody is an antibody comprising at least a human derived constant part such as a fully human antibody, a chimeric antibody and a humanized antibody.

In another preferred embodiment, the IgG3 antibody according to the present method is an IgG3 antibody with an increased therapeutic efficacy comprising an increased in vivo serum half life, preferably a serum half life of approximately 21 days, such as 19, 20, 21, 22, or 23 days.

According to the present invention, the present IgG3 antibody is preferably provided by:
(a) isolating a nucleic acid sequence encoding the heavy chain of an immunoglobulin G class 3 (IgG3) antibody;
(b) mutating the codon encoding amino acid position 435 to encode the amino acid residue histidine (H) to provide a mutated nucleic acid sequence;
(c) providing the mutated nucleic acid sequence with operable expression elements; and
(d) expressing the mutated nucleic acid and a nucleic acid sequence encoding the light chain of the immunoglobulin G class 3 (IgG3) antibody in a suitable host thereby providing a mutated immunoglobulin G class 3 (IgG3) antibody; and optionally
(e) isolating the mutated immunoglobulin G class 3 (IgG3) antibody.

Step (b) comprises mutating the codon encoding amino acid position 435 to encode the amino acid residue histidine (H) to provide a mutated nucleic acid sequence.

Depending on the preferred codon usage of the suitable host according to step (d), the skilled person is readily able to select the appropriate codon at position 435 encoding histidine. In general, for most higher eukaryotic or some yeast species as *Pichia pastoris*, step (b) will comprise mutating the codon encoding amino acid position 435 to CAC or CAT to provide the mutated nucleic acid sequence.

According to another aspect, the present invention relates to a mutated immunoglobulin G class 3 (IgG3) antibody, preferably a human antibody, wherein the mutation, as compared to the parent immunoglobulin G class 3 (IgG3) antibody, comprises a replacement of the amino acid arginine (R) at position 435 in the $C_H3$ domain with the amino acid histidine (H).

According to a preferred embodiment of this aspect, the present invention relates to a mutated immunoglobulin G class 3 (IgG3) antibody, preferably a human antibody, wherein the mutation, as compared to the parent immunoglobulin G class 3 (IgG3) antibody, consists of a replacement of the amino acid arginine (R) at position 435 in the $C_H3$ domain with the amino acid histidine (H).

Considering the improved therapeutic efficacy of the present IgG3 antibodies, and specifically their improved serum half life, the present invention, according to a third aspect, relates to mutated immunoglobulin G class 3 (IgG3) antibodies, as defined above, for use as a medicament, preferably for use as a medicament for immunotherapy such as, and preferably, rheumatoid arthritis, multiple sclerosis, psoriasis, and many forms of cancer including non-Hodgkin's lymphoma, colorectal cancer, head and neck cancer and breast cancer, and immune deficiencies.

Some immune deficiencies, such as X-linked agammaglobulinemia and hypogammaglobulinemia, result in partial or complete lack of antibodies. These diseases are often treated by inducing a short term form of immunity called passive immunity. Passive immunity is achieved through the transfer of ready-made antibodies in the form of human or animal serum, pooled immunoglobulin or monoclonal antibodies, into the affected individual. The present increased serum half life is especially suitable for treatment of these diseases.

The present invention will be further detailed and described using the following example wherein references is made to the appended figures wherein:

FIG. 1A: FcRn negative A375-WT cells did not show specific IgG transcytosis (IVIg) as it was comparable to passive leakage as measured by HRP transport. After transfection with the FcRn α-chain, A375-FcRn transports IgG from the apical to the basolateral compartment highly efficiently. When IVIg was mixed with Z-domain (minimal IgG-binding domain of Protein A) prior to transport at a 2:1 molar ratio (Z-domain:IgG) the IgG1 transport by A375-FcRn cells was significantly reduced, while IgG3 transport was enhanced.

FIG. 1B: JAR cells that naturally express FcRn, transported IgG1 and IgG3 from IVIg equally well. Incubation of IVIg with the Z-domain at a 2:1 molar ratio prior to transport inhibited transport of IgG1 but increased transport of IgG3.

100 µg/ml IVIg was used in both A) and B). IgG1 is shown in open bars, IgG3 in diagonally striped bars and HRP in black bars. The Y-axis represents the percentage of IgG transported from the apical compartment to the basolateral compartment. Statistical comparison was performed by one-way ANOVA followed by Tukey's Multiple Comparison Test and the level of significance is indicated as defined in the Materials and Methods section;

FIG. 2A: IgG3 and IgG1 were transcytozed equally well in A375-FcRn cells when transported separately from the apical to the basolateral compartment, and neither inhibited their own transport when the input was doubled. Yet in 1:1 mixtures, IgG3 transport was reduced in the presence of IgG1.

FIG. 2B: In JAR cells, IgG3 was efficiently transported from the apical to basolateral compartment when offered alone. The amount of either IgG1 or IgG3 transported was also unaffected by doubling the apical concentration, but IgG3 transport was inhibited by the presence of equal amounts of IgG1.

FIG. 2C: When only one subclass was present, A375-FcRn transported a fixed percentage of IgG from the apical to the basolateral side. Both for IgG1 and for IgG3 this percentage remained stable over the range tested.

Myeloma IgG1 and IMIg-derived IgG3 were used for all experiments. The data is the mean and standard deviation of three 3 independent experiments of 3 wells each. When both IgG1 and IgG3 were present, both were measured independently in the same sample. Transport of IgG3 in the presence of IgG1 was compared to transport of IgG3 alone by two-tailed t-test as indicated by brackets.

FIG. 3A: Apical to basolateral transport of recombinant IgG3 (10 µg/ml) in the absence or presence of increasing amounts of IgG1. IgG3 transport was inhibited up to a plateau when more than 1 ng/ml IgG1 was present. All data points were compared to the samples without IgG1 by one-way ANOVA and Dunnett's multiple comparison test FIG. 3B: Recombinant IgG3 alone (dotted line) or mixed with IgG1 (solid line) at a 1:1 ratio in increasing concentrations were added to the apical compartment and IgG3 was measured in the basolateral compartment. At concentrations lower than 1 µg/ml transport of IgG3 increased up to levels similar to those observed when IgG3 is transported alone.

All data points from mixed IgG1 and IgG3 transport were compared by t-test to the corresponding IgG3 transport without IgG1 present;

FIG. 4A: The crystal structure of FcRn with the Fc part of an IgG molecule, showing the orientation of the binding amino acid position 435 of IgG in yellow.

FIG. 4B: A close-up of the binding pocket, showing the side chain of amino acid 435 of IgG (histidine, shown in green) binding into the binding pocket in FcRn. When arginine was modelled into this position (shown in yellow) it protrudes into the FcRn surface area, possibly causing steric hinderance. The crystallographic coordinates where obtained from 17 and modelling was performed using VMD 1.8.4;

FIG. 5A: Mutating the amino acid at position 435 in IgG1 (H435) and in IgG3 (R435) to an alanine reduces transport, while exchanging the histidine native to IgG1 and the arginine native to IgG3 on each others backbone had no effect on their transport rate when offered separately to FcRn-transfected A375 cells.

FIG. 5B: While transport of IgG3-WT was inhibited by IgG1-WT, IgG1 bearing an alanine or an arginine at position 435 had no effect on IgG3 transport.

FIG. 5C: Transport of IgG3 with a histidine at position 435 was not inhibited by WT IgG1. When the amino acids found at position 435 in IgG1 and IgG3 were swapped, IgG1-H435R transport was inhibited by IgG3-R435H.

FIG. 5D: IgG1 and IgG3 were transported at equal levels when transported in the basolateral to apical direction, both when transported alone, and when mixed in a 1:1 ratio.

As indicated by +/−(IgG/no IgG), recombinant IgG1 and IgG3 was used separately in A) and the leftmost two bars in D), or mixed in B), C) and the two rightmost bars in D) at equal concentration (10 µg/ml/subclass). The presence of mutated variants (435H, 435A, 435R) is indicated by the corresponding letter. Transport of WT IgG was compared to transport of mutant IgG by one-way ANOVA with Dunnett's multiple comparison test and significance is indicated as described in the Materials and Methods section;

FIG. 6A: Approximately 95% of the total IgG added to apical compartments of confluent A375-FcRn monolayers was recovered after 24 hours from both the apical and the basolateral compartments when the IgG1 or IgG3 were added individually (10 µg/ml). However, when the IgG1 and IgG3 were mixed in equal amounts, approximately 65% of the initial IgG3 could be detected, suggesting IgG3 was degraded in the presence of IgG1. IgG1 recovery was similar to that found when no IgG3 was present. IgG3-R435H was not degraded in the presence of IgG1 as about 95% could be detected after 24 hours, similarly to IgG3 alone.

FIG. 6B: The relative concentration of IgG subclasses and the Histidine-435 containing IgG3 allotype G3m(s,t) in sera from patients with agammaglobulinemia patients four weeks after their last treatment with IVIg compared to IgG subclass and G3m(s,t) levels found in the corresponding IVIg preparation.

Data represents the average plus standard deviation calculated from measurements performed in serum from three patients. Statistical comparison was performed by one-way ANOVA followed by Tukey's Multiple Comparison Test and the level of significance is indicated as defined in the Materials and Methods section. For simplicity, significant differences are only displayed for IgG1 compared to all subclasses, and between IgG3 total and G3m(s,t) levels.

EXAMPLE

Introduction

In this example, the difference is demonstrated in FcRn mediated transport of IgG1 and IgG3. Using fully human in vitro and in vivo models, it was observed—unexpectedly—that IgG1 and IgG3 compete for FcRn-mediated transport and recycling. The present data demonstrate that the presence of an arginine at position 435 in IgG3 is sufficient to explain its high rate of catabolism observed in vivo.

Materials and Methods

Cell Culture:

Human choriocarcinoma cells (JAR, American Type Culture Collection, Manassas, Va. USA) were grown in IMDM medium (Cambrex, Verviers, Belgium), and melanoma cells (A375, FcRn-β2 m+, a kind gift from C. Sautes-Fridman and L. Cassard) in RPMI 1640 medium (Invitrogen/Gibco, Carlsbad, Calif.), both supplemented with L-glutamin (300 mg/ml, Invitrogen/Gibco), penicillin (100 U/ml, PAA Laboratories GmbH, Pasching, Germany), streptomycin (100 mg/ml, PAA) and 10% foetal calf serum (FCS, Bodinco, Alkmaar, The Netherlands). All cultures were carried out at 37° C., in saturated humidity and 5% $CO_2$ in air.

A375-FcRn

The cDNA of human FcRn was amplified by PCR using the forward 5' GGA TCC ACC ATG GGG GTC CCG CGG CCT CAG C 3' and the reverse 5' GAA TTC TCA GGC GGT GGC TGG AAT CAC 3' primer. The product was ligated into the pGEM-T vector (Invitrogen), and FcRn sequence was confirmed by automated DNA sequencing (ABI 373 Stretch automated sequencing machine, Applied Biosystems, Foster City, Calif., USA).

The BamHI-EcoRI fragment encompassing the complete FcRn coding region was subcloned into the pMX-puro vector (DNAX, Palo Alto, Calif., USA) and transfected together with a packaging vector into 293T-cells 42. Supernatants were used to transfect A375 cells. Expression of FcRn was confirmed by MAb 1G3 binding and quantitative RT-PCR.

IgG

Intravenous Immunoglobulin (IVIg, Sanquin, Amsterdam, The Netherlands) was purchased commercially. Myeloma IgG1 was obtained from three patients with multiple myeloma by serum protein precipitation and pooled.

Briefly, proteins were separated by DEAE size chromatography, after which IgG2, IgG3 and IgG4 were depleted by passing it over columns of sephadex-bound anti-subclass IgG. IgG3 was obtained from Intramuscular Ig (IMIg, Sanquin) by depleting other subclasses using protein A immobilised on a sepharose matrix.

Recombinant IgG1 and IgG3, both wild type and mutatant (IgG1H453A, IgG1-H435R, IgG3-R435A, IgG3-R435H) were produced in 293Freestyle cells (Invitrogen) according to the manufacturers instructions.

IgG1-H435A was generated as described. IgG1-H435R, IgG3-R435A and IgG3-R435H were generated using the Quickchange Site-directed-mutagenesis kit (Stratagene, La Jolla, Calif., USA) and the following oligonucleotide primers together with their reverse complementary primers:

```
IgG1-H435R:
GAG GCT CTG CAC AAC CGC TAC ACG CAG AAG AGC C

IgG3-R435A:
GAG GCT CTG CAC AAC GCC TAC ACG CAG AAG AGC C

IgG3-R435H:
GAG GCT CTG CAC AAC CAC TAC ACG CAG AAG AGC C
```

All mutations were confirmed by sequencing prior to expression.

Z Domain

The gene encoding the Z-domain was amplified by PCR from the vector pThio-His-ZZ 24 using the primers GGA TCC GTA GAC AAC AAA TTC AAC (forward) and CTG CAG TTA TTT CGG CGC CTG AGC ATC (reverse), simultaneously introducing restriction sites (NotI and BamHI), after which the PCR product was cloned into the pGEM-T vector (Promega, Madison, Wis., USA).

Using the BamHI and the NotI restriction sites, the gene was cloned into the pGEX 6.2 expression vector and the result verified by sequencing prior to expression in $E.\ coli$.

The GST tag was removed during purification using PreScision protease (GE healthcare) after which the Z-domain was allowed to run off the glutathione sepharose 4B column (GE healthcare, Chalfont St Giles, UK) by gravity flow. Finally, the eluate was dialysed against PBS.

IgG Transcytosis

For IgG transport experiments, 12 mm Transwell filters (0.4 mm pore size, Costar/Corning, Acton, Mass., USA) were inoculated with $5*10^5$ cells. Cells were grown overnight to confluence, washed with PBS and placed in a new 12-well plate with 1.5 ml medium in the basolateral and 0.5 ml in the apical compartment. The medium in the loading compartment contained IgG to be transported and 125 µg/ml streptavidin-HRP (Sanquin) to assess non-receptor-mediated transport or leakage.

Samples of 100 ml were taken from the appropriate compartment, and IgG was quantified. Apical to basolateral transport was calculated according to ([IgG]basolateral*1.5 ml)/ ([IgG]input*0.5 ml)*100%, and basolateral to apical transport as ([IgG]apical*0.5 ml)/([IgG]input*1.5 ml)*100%. All experiments were performed in triplicate.

Agammaglobulinemia Patients

Serum samples from 3 patients suffering from agammaglobulinemia who are regularly treated with IVIg at 4 week interval, were taken 4 weeks after receiving IVIg and IgG levels measured as described below. Informed consent was obtained from all patient.

IgG Quantification

IgG subclass concentrations in serum samples were determined by Nephelometry (Behringer Nephelometer II, Behringer diagnostics, Deerfield, Ill., USA) according to manufacturers protocols. In all other cases, IgG concentrations were determined by sandwich ELISA.

Subclass specific mouse monoclonal antibodies (IgG1: MH 161-1; IgG3: MH163-1, Sanquin) or allotype specific monoclonal anti G3m(t) (15A10, Sanquin) were used to capture G3m(s,t) IgG3 as both G3m(s) and the G3m(t) occur almost exclusively together, and because G3m(t) is rarely found without G3m(s). A mouse monoclonal anti-IgG-HRP (Southern Biotech, Birmingham, Ala., USA) was used for detection in all assays except the G3m(s,t) ELISA where mouse monoclonal anti-IgG3-HRP (MH163-1, Sanquin) was used.

Conversion of 3,3',5,5'-Tetramethylbenzidine (TMB) was used to quantitate HRP activity and absorptions were read using a Genios Pro plate reader (Tecan, Männedorf, Switzerland) at 450 nm. The standard curves were made using the same IgG preparations used for transport or to treat patients.

Statistical Analysis and Data Sets

All presented data represent the mean and standard deviation of at least 3 independent experiments each consisting of 3 replicates. GraphPad Prism version 4.00 for Windows (GraphPad Software, San Diego Calif., USA) was used for all statistical analysis. Significance was set at p=0.05, and the level of significance is indicated on all figures as *: p=0.05; : p=0.01; *: p=0.001.

Results

FcRn-Mediated IgG-Transport

Figure 1:
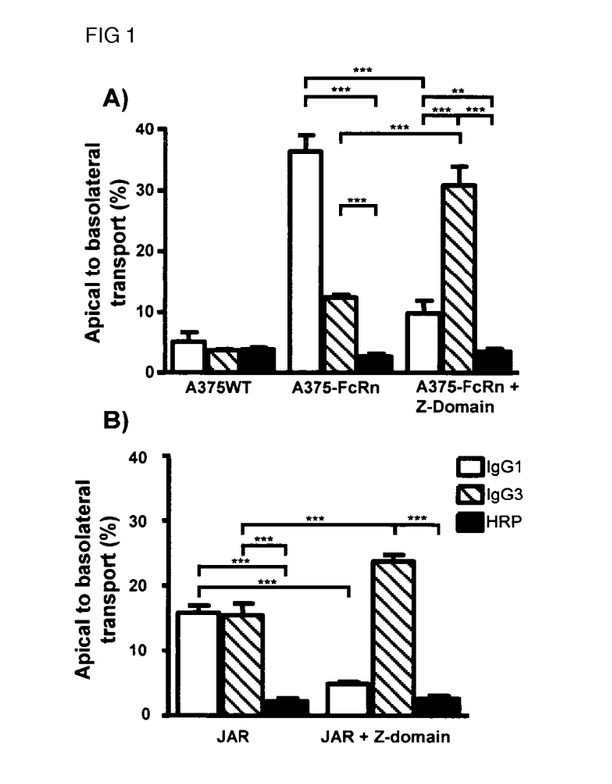
FIG. 1: shows that FcRn mediated transport of IVIg in JAR and A375 is inhibited by Z-domains for IgG1 but not for IgG3.

The FcRn-negative human cell line A375 was unable to transport significant amounts of IgG from the apical to the basolateral compartment (FIG. 1A). After transduction with the FcRn alpha chain gene (A375-FcRn), these cells actively transported IgG across a mono layer. In addition, IgG transport across placental syncytiotrophoblast derived JAR cells expressing endogenous FcRn was studied (FIG. 1B).

For these studies IVIg, a polyclonal mix of all human IgG subtypes in physiological ratios (approximately 60% IgG1, 33% IgG2, 3% IgG3, 3% IgG4) was used. Transport of all subclasses was observed, yet we found that A375-FcRn transported 3 to 4 times more IgG1 than IgG3, while JAR transports equal amounts of both.

*Staphylococcus* Protein A binds all IgG subclasses except IgG3 at the same site as FcRn. A competitive inhibitor of IgG1, IgG2 and IgG4 for binding to FcRn was generated using a minimal binding domain of protein A (the Z-domain, a triple alpha helix structure of 59 amino acids).

When IVIg was incubated with this Z-domain prior to transport experiments, it was found that using a molar ratio as low as the theoretical minimum of 2:1 (Z:IgG), transport of IgG1 by A375-FcRn cells was reduced to levels approaching those of A375-WT (FIG. 1A).

Similarly, in the presence of Z-domains the IgG1-transport by JAR cells was reduced to levels observed for nonspecific transport (FIG. 1B), demonstrating IgG1 transport to be FcRn dependent in both cell types.

Remarkably, IgG3 transport was significantly increased, both in JAR cells and in A375-FcRn cells, upon inhibiting FcRn-mediated transport of other subclasses using the Z-domain (FIGS. 1A and 1B) indicating that active transport of the other IgG subclasses interfered with IgG3 transport.

IgG1 Interferes with IgG3 Transport

Figure 2:
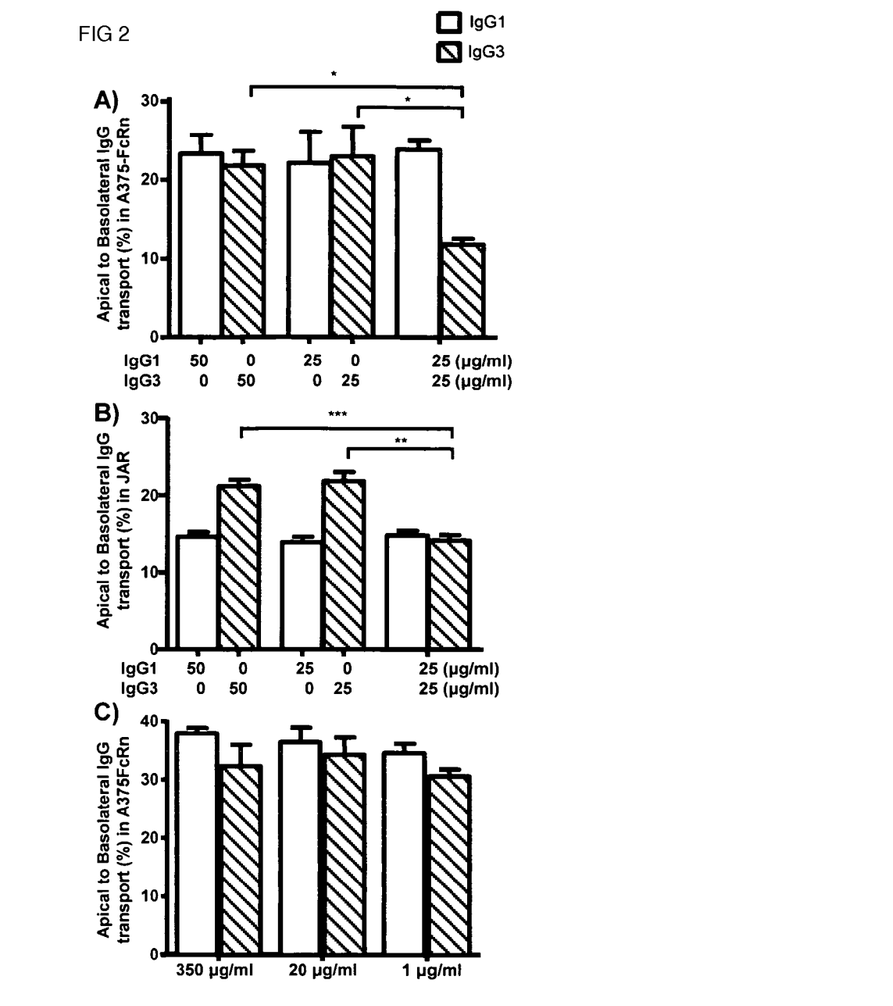
FIG. 2: shows that IgG3 transport is inhibited by IgG1 at non-saturating conditions.

In agreement with this finding, it was observed that when myeloma IgG1 or IgG3 were offered separately to A375-FcRn, IgG1 and IgG3 were transported in equal amounts (FIG. 2A). JAR cells even transported up to 50% more IgG3 than IgG1 when offered individually (FIG. 2B). However, when an equimolar mixture of IgG1 and IgG3 was offered, IgG3 transport by A375-FcRn and JAR was reduced to similar levels as seen in IVIG transport experiments (FIGS. 2A and 2B).

It was tested if this was due to saturation of FcRn but no evidence was found for this, as reducing or increasing the concentration of purified IgG1 or IgG3 over a large range (1 μg/ml-350 μg/ml) did not affect the relative transport efficiency (FIG. 2C).

Concentration Dependent Inhibition of IgG3 Transport by IgG1

Figure 3:
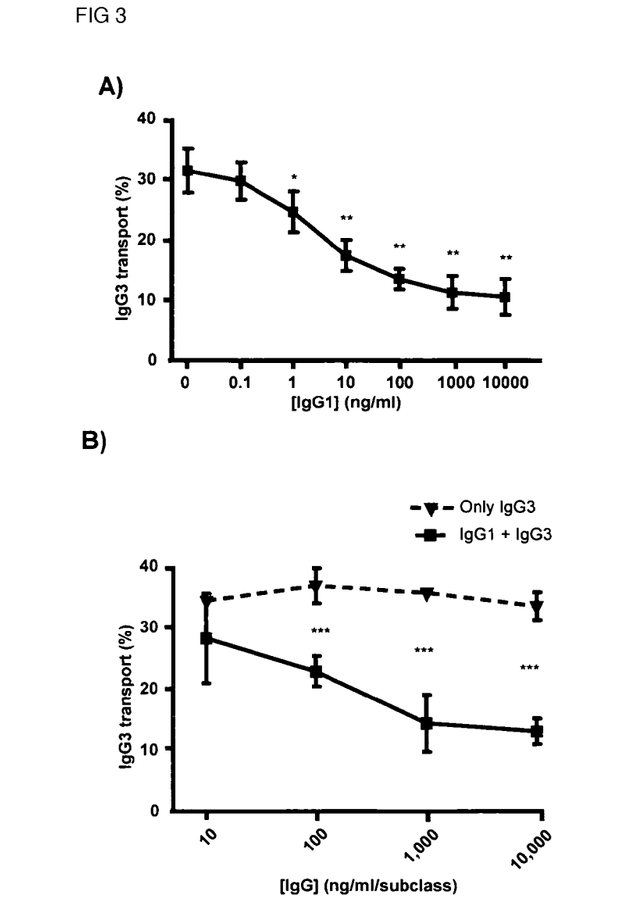
FIG. 3: shows concentration-dependent inhibition of IgG3 transport by IgG1.

Identical results were obtained using V-gene matched recombinant IgG1 and IgG3. When the IgG3 concentration was kept constant at 10 μg/ml, apical to basolateral IgG3 transport was significantly ($p<0.05$) reduced at IgG1 concentrations as low as 1 ng/ml (FIG. 3A). When IgG1 and IgG3 were mixed in equimolar ratio's, the relative IgG3 transport was significantly reduced compared to transport of IgG3 alone. The inhibition of IgG3 transport was concentration dependent and was lost at IgG concentrations of 10 ng/ml/subclass (FIG. 3B). Remarkably, the same concentration of IgG1 (10 ng/ml) did significantly inhibit a 1000 fold excess of IgG3 (10 μg/ml, FIG. 3A).

These data demonstrated that the inhibition exerted by IgG1 on IgG3 during apical to basolateral transcytosis is concentration dependant, and suggested that the two subclasses compete for FcRn-mediated transport.

The Inhibition of IgG3 Transport by IgG1 is Due to R435

Figure 4:
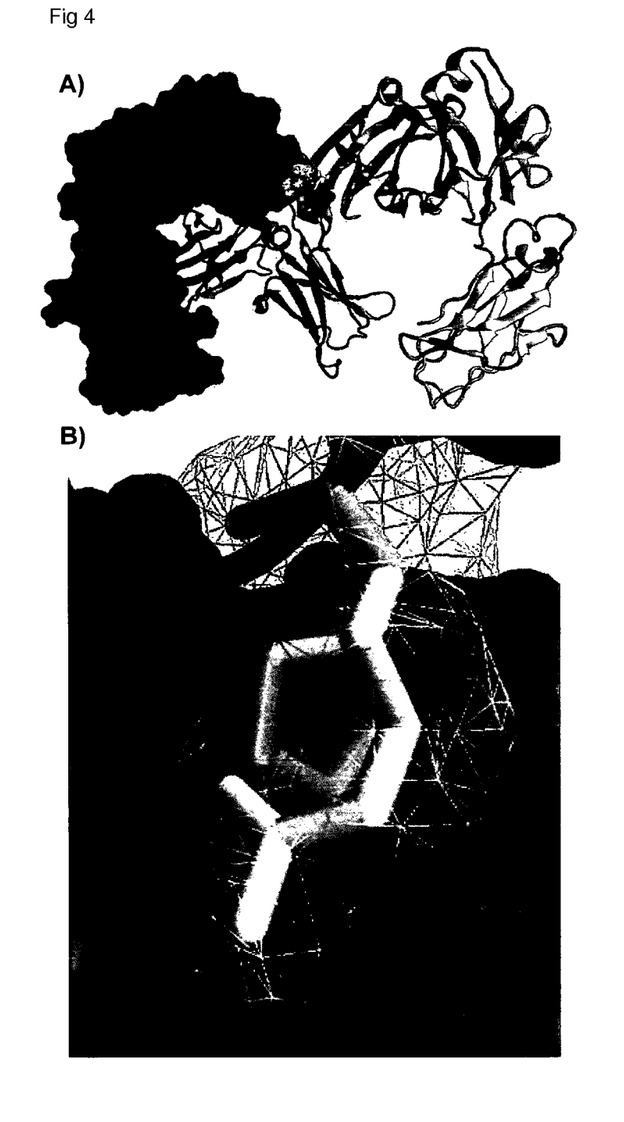
FIG. 4: shows the crystal structure of rat FcRn with Fc with arginine modelled at position 435.

IgG3 contains an arginine at position 435, instead of the histidine found in the other IgG subclasses. When these differences were modeled into the existing crystal structure it was clear that the longer side chain of arginine may potentially disrupt the tight fit of IgG in the FcRn binding pocket (FIG. 4), although it may also theoretically convey a more favorable charge at pH 7.5, at which the histidine is neutral but arginine is positively charged.

When the amino acid at position 435 was mutated to an alanine, almost all FcRn-dependent transport was abrogated (FIG. 5A) and when the histidine at position 310 was also mutated to an alanine, no specific IgG transport was seen (data not shown).

IgG1 was also mutated to include the IgG3-derived arginine residue and vice versa (IgG1-H435R and IgG3-R435H, respectively). These mutations did not significantly influence transport efficiency of either subclass when transported individually (FIG. 5A).

Since the presence of IgG1-WT resulted in reduced transport efficiency for IgG3-WT, various IgG1 and IgG3 variants bearing mutations at position 435 were mixed in 1:1 ratios.

IgG1-H435A, which bound FcRn inefficiently, was hardly transcytosed by FcRn (FIG. 5A), and was also unable to inhibit transport of IgG3 (FIG. 5B). Importantly, transport competent IgG1-H435R (FIG. 5A) was unable to inhibit IgG3 transport (FIG. 5B), indicating the arginine/histidine difference between IgG3 and IgG1 to be important for IgG1-mediated inhibition of IgG3 transport.

Likewise, the level of IgG3-R435H transport was unaffected by the presence of equal amounts of any of the IgG1 variants (IgG1-WT, IgG1-H435A or IgG1-H435R) (FIG. 5C).

Remarkably, IgG3-R435H did inhibit transport of IgG1-H435R (FIG. 5C) to a similar extent as IgG1-WT inhibited transport of IgG3-WT (FIG. 5B), demonstrating that R435 allows for FcRn-mediated binding and efficient transport, but not when H435-containing IgG is present.

Figure 5:
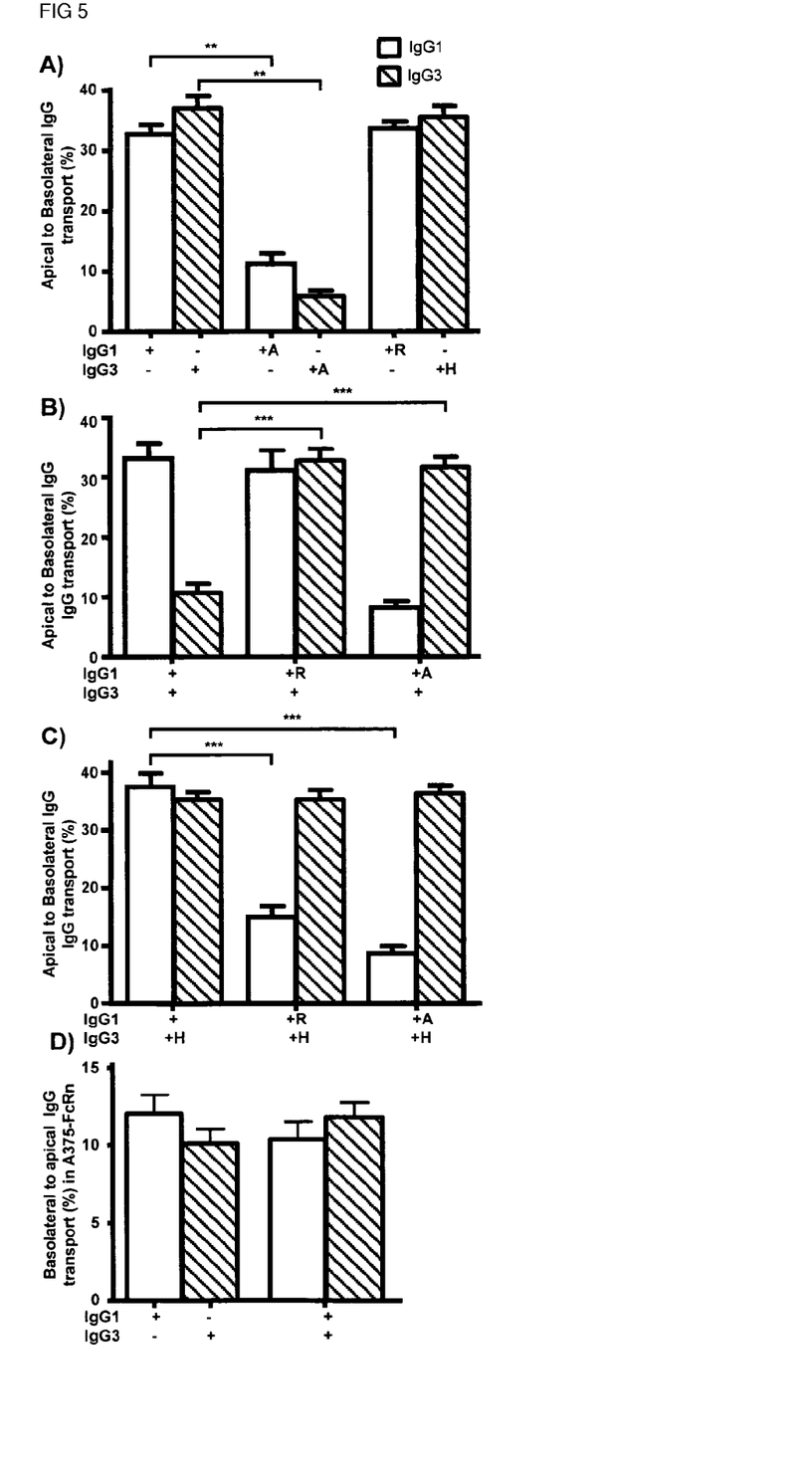
FIG. 5: shows that apical to basolateral transport of IgG with an arginine at position 435 is inhibited by IgG with a histidine on position 435, whereas basolateral to apical transport in unaffected.

In the basolateral to apical direction, however, IgG1 did not influence IgG3 transport (FIG. 5D). Thus, IgG1 inhibited only apical to basolateral FcRn-mediated IgG3 transport (FIGS. 1 to 5).

Degradation In Vitro

Figure 6:
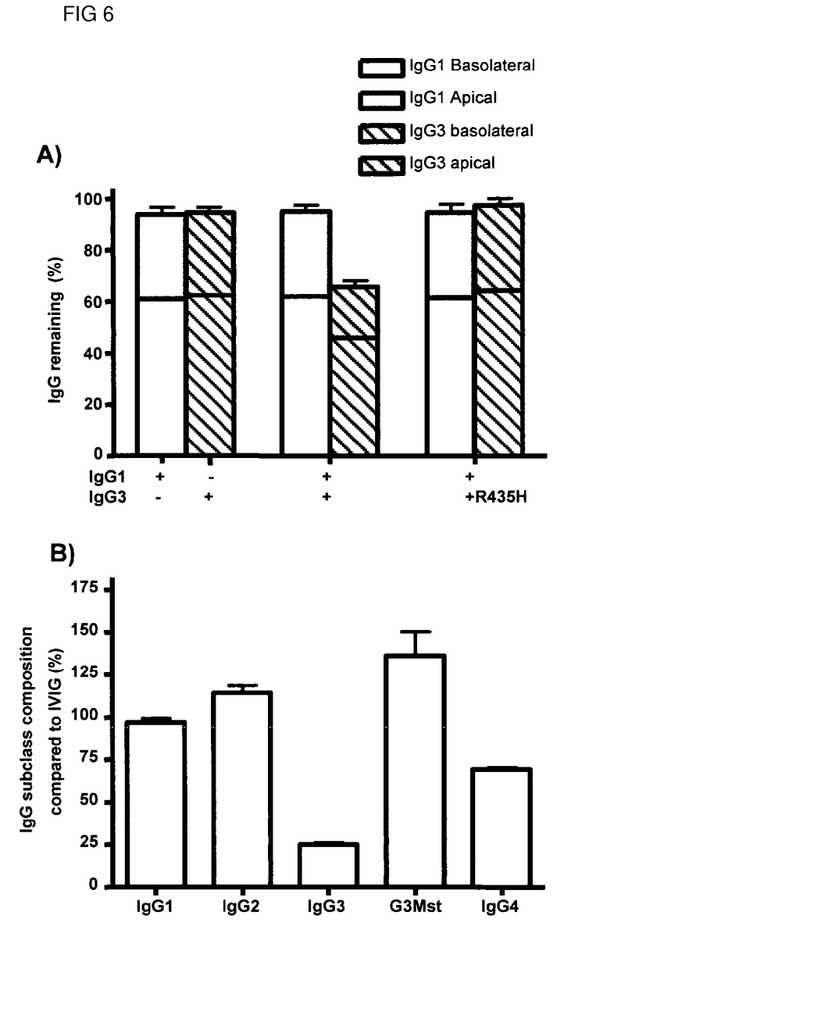
FIG. 6: shows that enhanced catabolism of IgG3 is due to R435 in vivo and in vitro.

Since FcRn is responsible for rescuing IgG from lysosomal degradation, it was tested if the reduced IgG3 transport in the presence of IgG1 resulted in its enhanced degradation during apical to basolateral transport. After 24 hours, large differences were observed in the recovery of different IgG variants from the apical and basolateral compartments (FIG. 6).

Up to 95% of IgG1-WT or IgG3-WT could be accounted for when they were transported alone, yet when they were mixed in equimolar amounts (10 μg/ml/subclass), all IgG1 was recovered, but only 60% of the initial amount of IgG3 could be detected.

However, when IgG1-WT and IgG3-R435H were offered at equal concentrations, recovery of both IgG1-WT and IgG3-R435H was around 95% (FIG. 6), indicating that the decreased transport and enhanced loss of IgG3 in the presence of IgG1 was solely due to the arginine at position 435.

In agreement with the reduced transport inhibition of IgG3 by IgG1 at lower concentrations (FIG. 3), a concentration-dependent decrease in IgG3 degradation was observed when IgG3 was transported together with IgG1 at low concentrations (10 ng/ml/subclass, data not shown). Reduced transport efficiency therefore is associated with more rapid degradation, likely due to loss of FcRn-mediated rescue.

Enhanced Half-Life of Histidine-435 Containing IgG3 In Vivo

To investigate whether R435 present in IgG3 is also the cause of the low half life of IgG3 in vivo, the serum persistence of different IVIg-derived IgG3 allotypes were compared in the serum of X-linked agammaglobulinemic patients.

Four weeks after the last injection of IVIg, the relative amounts of IgG1 and IgG2 were unchanged in these patients compared to the amounts found in the IVIg preparation itself (FIG. 6B). As expected, the total IgG3 level was significantly lowered, but the relative amount remaining of IgG3 of the G3m(s,t) allotype was significantly increased. Thus, natural variants of IgG3 containing an histidine or an arginine at position 435 exhibit a low or high rate of catabolism, respectively.

Together these data indicate R435 found in the more commonly found allotypic forms (G3m(b), G3m(g)) to be sufficient to explain their high rate of catabolism in vivo.

Discussion

IgG is transported efficiently across the human placenta and the half life of IgG is extended compared to that of similar sized serum proteins due to a single receptor, FcRn. The only exception to this is human IgG3, which has been described as having a half life that is comparable to non-FcRn binding proteins. Conversely, maternally-derived IgG3 is found in neonates, although at considerable lower levels than IgG1 relative to maternal levels.

Observers of both phenomena have sought an explanation in subtle differences between IgG1 and IgG3, as discussed below, but without clear experimental evidence. In this example, FcRn-mediated transport of purified IgG3 was found to be normal, but an unexpected inhibition of IgG3 transport in the presence of other IgG subclasses was found.

This inhibition was found to be due to a single amino acid difference between IgG3 and the other IgG subclasses, and it correlated directly with degradation of IgG3 in vitro and enhanced catabolism in vivo.

In the present example, human placenta-derived JAR cells, which naturally express FcRn, human A375 cells, which are devoid of FcRn-expression, and A375 cells transfected with human FcRn were used to study human IgG transport in an entirely human system, thus eliminating any cross-species incompatibilities.

Particularly studied were the differences between FcRn mediated transport of IgG1 and IgG3, and the effect of the amino acid differences at position 435. Various sources of IgG were used: IVIg, myeloma IgG, and V-gene matched recombinant wild type IgG1 and IgG3 and mutated variants thereof differing only at position 435.

The transport rates of purified IgG1 and IgG3 were similar for all IgG sources in both cell lines, except that IgG3 transport was relatively higher in the JAR cells, suggesting that although FcRn was required for transport, another FcR might be involved. However, when IgG1 and IgG3 were transported simultaneously, the transport of IgG3 was found to be inhibited by IgG1 in both cell types.

This inhibition was observed for myeloma IgG1 combined with IgG3 purified from IMIg, for V-gene matched recombinant IgGs, and for IVIg in which the inhibition could be alleviated by a protein A based inhibitor of FcRn-IgG binding (Z-domain) specific for IgG1, IgG2 and IgG4.

By using well defined recombinant antibodies, the possibility was excluded that the observed inhibition was linked to artefacts caused by differences in the variable region, light chain isotype or by contamination of the antibody preparations with other subclasses.

FcRn-saturation was ruled out as a possible explanation for the observed inhibition, as the relative amount of IgG transported was constant over a wide range of input concentrations of both purified IgG1 and IgG3 for both cell types studied.

The presence or absence of IgG3 also had no effect on IgG1 transport. The IgG1-induced inhibition of IgG3 transport was dose dependent and increased along a sigmoid curve, requiring a relative low amount of IgG1.

It was found that mutating the amino acid at position 435, from a histidine to an arginine or an alanine in IgG1, or from an arginine to a histidine in IgG3, abrogated the inhibition of FcRn-mediated IgG3 transport by IgG1. This inhibition could even be completely reversed by swapping the amino acids in position 435 (histidine/arginine) between IgG1/IgG3 (resulting in IgG1-H435R and IgG3-R435H). Mutating position 435 to an alanine reduced transport almost to background levels for both IgG1 and IgG3.

CONCLUSION

IgG3 is known for both it equal or superior effector functions compared to IgG1—the most commonly used isotype used for immunotherapy—but also for its short in vivo half life.

For the latter part, the present data shows that R435-containing IgG3 looses the competition for FcRn binding and routing from the lysosomal pathway explaining the high catabolism in vivo and relative low transport of IgG3 across the placenta.

The present data demonstrate that both FcRn-mediated effects can be alleviated by replacing the R435 with a histidine. This has important implications for current and future antibody-based therapies aimed at maximal effector functions.

The invention claimed is:

1. A method for increasing the in vivo half life of an immunoglobulin G class 3 (IgG3) antibody comprising providing a mutated immunoglobulin G class 3 (IgG3) antibody, wherein the mutation, as compared to the parent immunoglobulin G class 3 (IgG3) antibody, consists of a replacement of the amino acid arginine (R) at position 435 in the $C_H3$ domain with the amino acid histidine (H).

2. A method according to claim 1, wherein the immunoglobulin G class 3 (IgG3) antibody is a human immunoglobulin G class 3 (IgG3) antibody.

3. A method according to claim 1, wherein providing a mutated immunoglobulin G class 3 (IgG3) antibody comprises:

a) isolating a nucleic acid sequence encoding the heavy chain of an immunoglobulin G class 3 (IgG3) antibody;
b) mutating the codon encoding amino acid position 435 to encode the amino acid residue histidine (H) to provide a mutated nucleic acid sequence;
c) providing the mutated nucleic acid sequence with operable expression elements; and
d) expressing the mutated nucleic acid and a nucleic acid sequence encoding the light chain of the immunoglobulin G class 3 (IgG3) antibody in a suitable host thereby providing a mutated immunoglobulin G class 3 (IgG3) antibody; and optionally
e) isolating the mutated immunoglobulin G class 3 (IgG3) antibody.

* * * * *